United States Patent
Hamer et al.

(10) Patent No.: US 10,788,476 B2
(45) Date of Patent: Sep. 29, 2020

(54) FRICTION TESTING APPARATUS AND METHOD

(71) Applicant: PCS Instruments Ltd, London (GB)

(72) Inventors: Clive Hamer, London (GB); John Hutchinson, London (GB)

(73) Assignee: PCS INSTRUMENTS LTD, London (GB)

( * ) Notice: Subject to any disclaimer, the term of this patent is extended or adjusted under 35 U.S.C. 154(b) by 166 days.

(21) Appl. No.: 15/774,729

(22) PCT Filed: Nov. 15, 2016

(86) PCT No.: PCT/EP2016/077693
§ 371 (c)(1),
(2) Date: May 9, 2018

(87) PCT Pub. No.: WO2017/097549
PCT Pub. Date: Jun. 15, 2017

(65) Prior Publication Data
US 2018/0321216 A1 Nov. 8, 2018

(30) Foreign Application Priority Data
Dec. 7, 2015 (GB) .................................. 1520619.6

(51) Int. Cl.
*G01N 33/30* (2006.01)
*G01N 19/02* (2006.01)
(Continued)

(52) U.S. Cl.
CPC ............ *G01N 33/30* (2013.01); *G01N 3/56* (2013.01); *G01N 11/00* (2013.01); *G01N 11/16* (2013.01); *G01N 19/02* (2013.01)

(58) Field of Classification Search
None
See application file for complete search history.

(56) References Cited

U.S. PATENT DOCUMENTS

| | | | | |
|---|---|---|---|---|
| 2,883,855 A | * | 4/1959 | Spengler | G01N 33/30 73/10 |
| 3,823,599 A | * | 7/1974 | Litz | G01N 19/02 73/10 |

(Continued)

FOREIGN PATENT DOCUMENTS

| | | |
|---|---|---|
| GB | 2 263 553 A | 7/1993 |
| GB | 2 270 387 A | 3/1994 |
| WO | WO 2012/006613 A2 | 1/2012 |

OTHER PUBLICATIONS

International Search Report and Written Opinion for PCT/EP2016/077693 dated Jan. 23, 2017, 12 pages.

*Primary Examiner* — Paul M. West
*Assistant Examiner* — Mark A Shabman
(74) *Attorney, Agent, or Firm* — Fay Sharpe LLP

(57) ABSTRACT

The invention relates to a test method and apparatus for measuring the frictional properties of a fluid and comprises; a first specimen holder which is adapted to hold a first specimen in the fluid being tested in contact with a second specimen surface of a second specimen in a second specimen holder, with means for applying a measurable load between the two specimens, and with oscillatory driving means for oscillating at least one of the specimen holders along a first direction, and a motion inducing means, for inducing a motion between the first and second specimen holders in a second direction to induce a compound movement between the specimens which has been found results in more accurate readings. The first specimen holder is connected to a shaft which is induced to move in the first direction being the direction of the length of the shaft and the motion inducing means for inducing a motion in a second direction may be an off-centre counter weight located on the shaft.

12 Claims, 4 Drawing Sheets

(51) Int. Cl.
    *G01N 3/56*     (2006.01)
    *G01N 11/00*     (2006.01)
    *G01N 11/16*     (2006.01)

(56) References Cited

U.S. PATENT DOCUMENTS

| | | | |
|---|---|---|---|
| 5,377,525 A * | 1/1995 | Hutchinson | G01N 19/02 73/10 |
| 5,388,442 A * | 2/1995 | Kumar | G01N 19/02 73/10 |
| 6,349,587 B1 * | 2/2002 | Mani | G01N 19/02 73/9 |
| 6,401,058 B1 * | 6/2002 | Akalin | G01M 13/005 702/34 |
| 8,151,625 B2 * | 4/2012 | Ebrecht | G01N 19/02 73/9 |

\* cited by examiner

FRICTION TESTING APPARATUS AND METHOD

CROSS-REFERENCE TO RELATED APPLICATIONS

This application is a National Stage Entry of PCT/EP2016/077693, and claims priority to, and the benefit of, Great Britain Patent Application No. GB 1520619.6, filed Dec. 7, 2015, the entirety of which is hereby incorporated by reference as if fully set forth herein.

BACKGROUND

This invention relates to apparatus and method for testing the lubricating properties of lubricants or other fluids and/or the frictional and wear properties of materials. Such apparatus simulate the conditions of operation of a mechanical device having moving parts and a fluid lubricant, such as for example a fuel pump. Measurements can be made of the condition of the lubricant, or other fluid under test, the condition of the moving parts and the forces acting on the moving parts during the test. From these measurements it is typically possible to test new materials and lubricants or other fluids before sale as new products or before introduction into new products as components.

An important feature of such testing machines is that they reproduce reliable results for a range of test fluids. The results are dependent on the reliability of the wear on the test sample which needs to be accurately correlated with the properties of the test fluid and not any other extraneous factors.

A previous disclosure UK patent No 2270387 describes an apparatus for testing lubricity using a rigid push rod. In this disclosure the objective is to reduce unwanted vibration, caused by the frequency and displacement amplitude of the oscillating masses and not on the load, since, when tests are carried out at low loads even very small unwanted vibrations can completely swamp the frictional forces of interest. This is solved by connecting the support measuring means to a support mass which is at least ten times as great as the combined mass of the oscillating arm and the specimen holder.

Another apparent problem with known devices is that they give rise to problems of stroke length consistency under conditions of varying friction coefficient between the test specimens, especially at stroke lengths of less than 0.1 mm. The frictional forces generated in a sliding contact are inherently non-linear with respect to the sliding velocity or displacement. This means that at short stroke lengths there is a tendency for stick-slip behaviour to occur, which can be difficult to control. Known apparatus which use mechanical linkages to drive the moving specimen do not suffer from this problem but cumulative tolerance errors in the linkage mean that accurate short stroke lengths are again difficult to achieve with good reproducibility. Prior solutions have sought to stiffen the drive components to alleviate this problem.

STATEMENT OF INVENTION

According to the invention there is provided a test apparatus and method according to the appended claims.

DESCRIPTION OF FIGURES

The invention is illustrated, merely by way of example, in the accompanying drawings in which.

DETAILED DESCRIPTION

Figure 1:
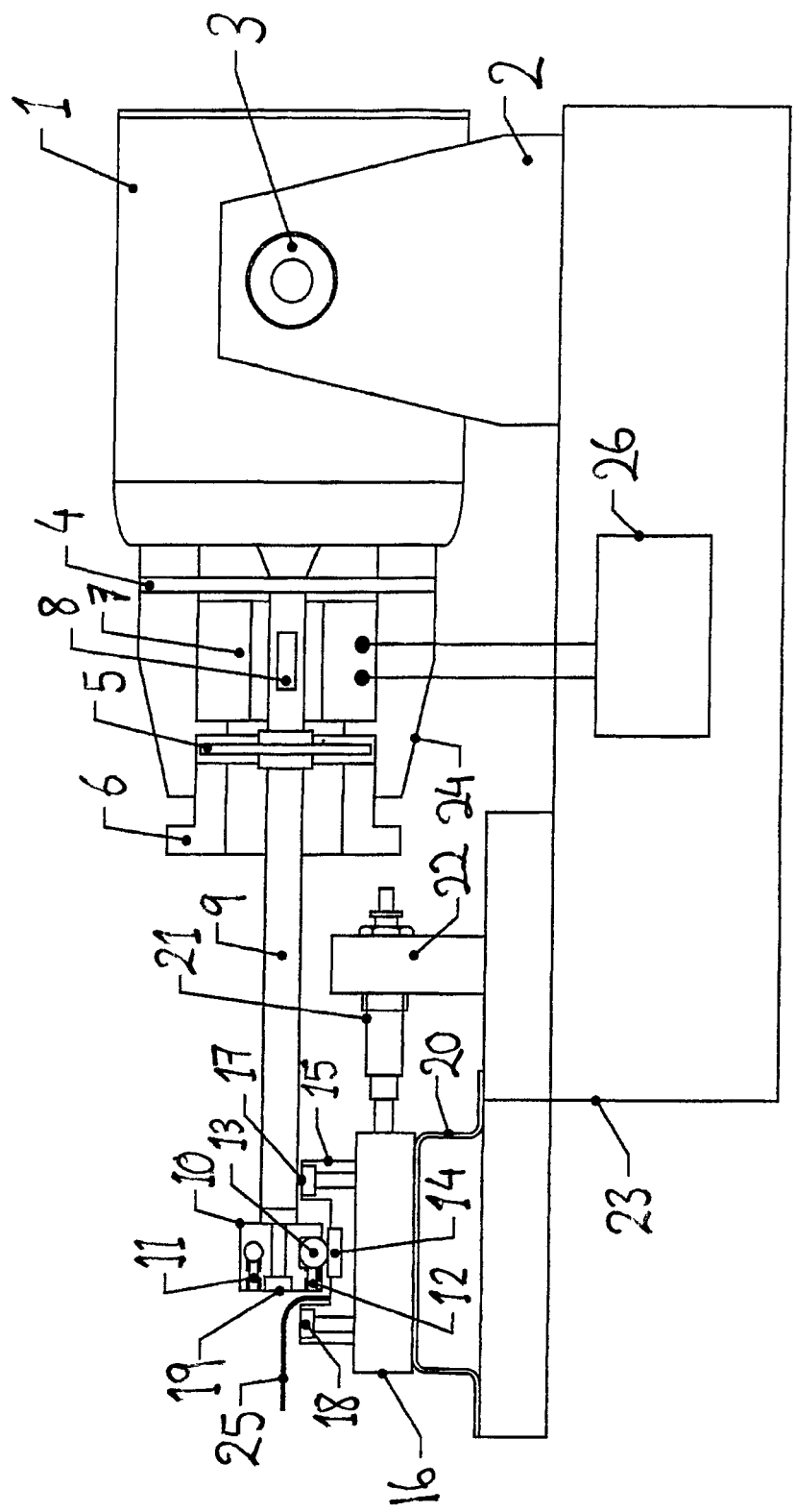
FIG. 1 is a part longitudinal section of an embodiment of the apparatus in accordance with the invention taken along the line I-I in FIG. 2.
Figure 2:
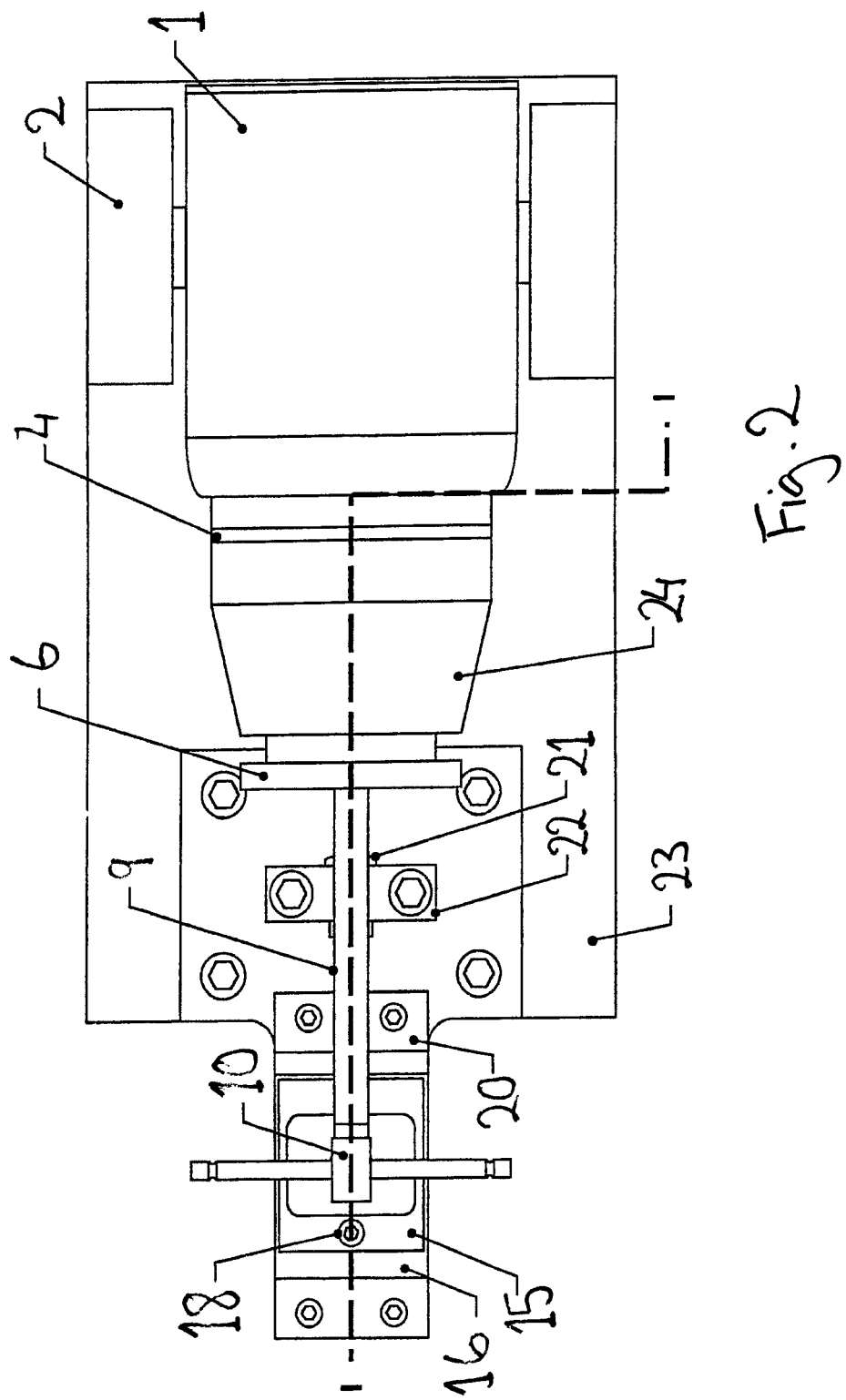
FIG. 2 is a plan view of one embodiment of the apparatus in accordance with the invention.

Referring to the drawings, there is shown one embodiment of a test apparatus according to the present invention having upper and lower specimens 13 and 14 respectively. The upper specimen 13 is releasedly held in the upper specimen holder 10 by a grub screw 12. The upper specimen 13 comprises a sphere of the material under test. The upper specimen holder 10 is releasedly attached by a screw 19 to a push rod 9 connected to the electromagnetic vibrator 1. The push rod 9 is in the form of a hollow tube of any suitable material with a measureable elasticity.

In this embodiment a rear flexure 4 is attached to the push rod 9 and clamped around its outside edge in housing 24. The rear flexure 4 acts to control the axial stiffness of the vibrator 1. A forward flexure 5 is designed to be about 10 times stiffer in the axial direction than the rear flexure 4 and is attached to the push rod 9 but free at its outside edge when operating at stroke lengths of more than 0.2 mm.

The displacement measuring means will typically be a Linear Variable Differential Transformer (LVDT) which will be incorporated into an electrical feedback circuit to control the amplitude of oscillation of the vibrator. Conveniently one or more flexures may be incorporated along the axis of oscillation of the vibrator and specimen holder such that the flexures resist the oscillation of the specimen holder. These flexures may comprise a spring stiffness only, or a spring and damper in parallel, or a damper only. The flexures apply a resistance to the motion of the movable specimen holder which is axial with respect to displacement and/or velocity. Thus a change of, for example 50% in the frictional force between the specimens will only result in a change of approximately 5% in the total load experienced by the vibrator. The effect is thus to reduce the sensitivity of the stroke length to changes in the axial frictional load and allow reliable operation at very short stroke lengths.

When it is desired to operate the vibrator 1 at stroke lengths of less than 0.2 mm, for example when carrying out fretting tests, the threaded collar 6 is screwed into housing 24, clamping the outside edge of forward flexure 5 against the housing 24 and thus increasing the axial stiffness of the vibrator 1 by about 10 times. This permits reliable operation at stroke lengths of 10 microns or less.

In order to measure and control the stroke length of the vibrator 1 a linear variable differential transformer (LVDT) 7 is held in housing 24 with the push rod 9 running through its centre. The LVDT core 8 is held rigidly inside the push rod 9 so that it is axially and longitudinally central inside the LVDT 7 when the push rod 9 is at rest. The push rod 9 is preferably made of non-magnetic material to allow the LVDT 7 to operate correctly. In use the LVDT 7 detects the motion of the core 8 and hence the push rod 9 and upper specimen holder 10 and a feedback control circuit 26 is used to regulate the power to the vibrator to maintain the stroke length at any desired value, irrespective of changes in the friction coefficient between the specimens.

The vibrator 1 is pivoted on two bearings 3 held in supports 2. The base block 23 is designed to be approximately 500 times more massive than the total mass of all the oscillating components of the apparatus. This is easy to achieve whilst keeping the total mass of the apparatus low enough to be hand portable because the total oscillating mass is only about 40 grams. This ensures that the inertial forces reacted against the vibrator 1 by the oscillating masses will only give rise to tiny accelerations in the body of the apparatus and do not disturb the measurements of friction force.

Load is applied to the specimens by means of dead weights suspended from load pin 11. Alternatively an adjustable spring balance system could be used. The lower specimen 14 is releasedly clamped into the lower specimen holder 15. This specimen holder is in the form of a small stainless steel bath which can contain a small volume of test lubricant. The specimen holder is releasedly clamped onto the heater block 16 by screws 17 and 18.

Figure 3:
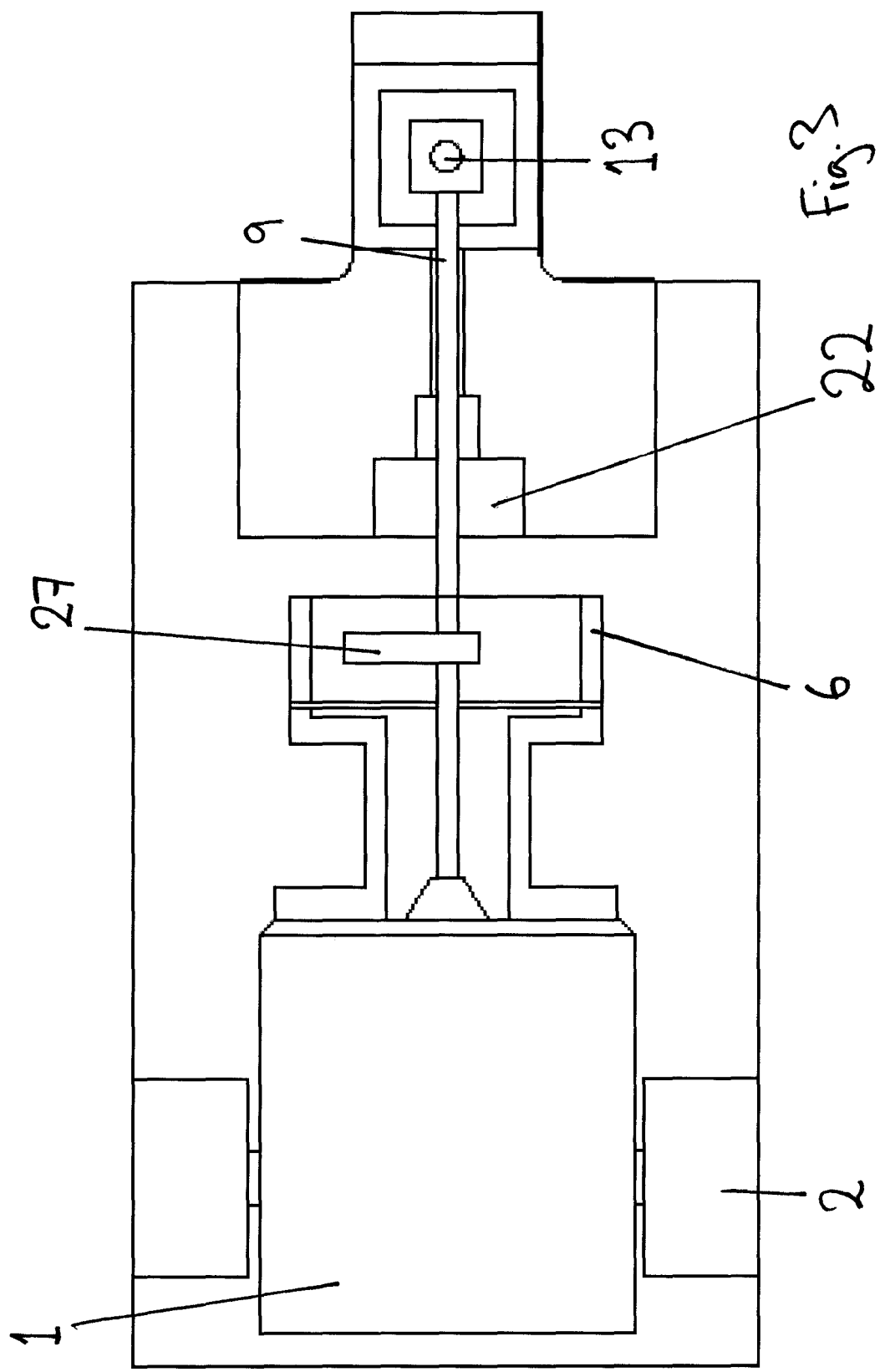
FIG. 3 is a simplified plan view of a further embodiment of the apparatus in accordance with the invention.
Figure 4:
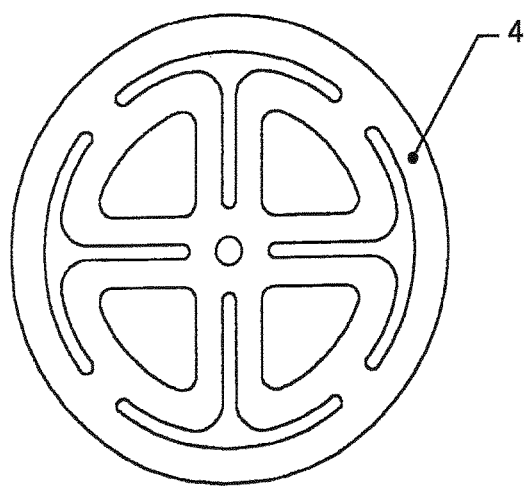
FIG. 4 is a cross section through a flexural member of a further embodiment of the invention.
Figure 5:
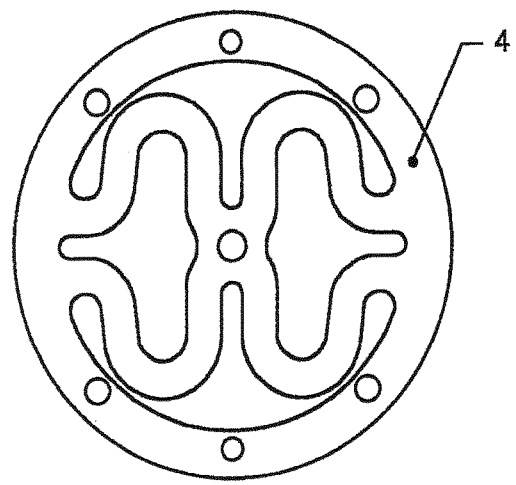
FIG. 5 is a cross section through a flexural member of a further embodiment of the invention.

Referring now to FIG. 3, there is provided an eccentric counter weight 27, fixedly attached to the push rod 9 located within the threaded collar 6. This eccentric counter weight 27 has an asymmetrical weight distribution with respect to the centre line of the push rod 9 which has the effect of inducing a radial oscillation of the push rod 9 in a direction orthogonal to the axial vibrational movement and correspondingly the upper specimen holder 10 to oscillate the sample in radial motion in addition to the primary axial motion induced by the vibrator 1.

The stiffness of the push rod can be adjusted, for example to reduce the stiffness to increase the effect of the radial vibration.

Following each test the wear indication or wear scar on either or both of the upper lower specimen 13 and lower specimen 14 is measured in width, length and depth dimensions and this correlates with the frictional properties of the fluid being tested. This compound movement of the upper specimen holder 10 relative to the lower specimen holder 15 in both the axial and non-axial or radial directions, has surprisingly been found to provide more consistent results representing a truer and more accurate correlation to the frictional properties of the fluid being tested.

This non-axial component of the movement of the push rod 9 and upper specimen holder 10, could be induced by alternative means such as provided by a separate mechanical or electrical motive force in addition to the vibrator 1. In this embodiment the non-axial component of the movement of the push rod 9 is in a radial direction, which is orthogonal to the first axial direction of movement of the pushrod. In alternative embodiments it may be possible to induce movement in the second direction in directions other than orthogonally to the first direction and still achieve the desirable results.

The counter weight 27 is located approximately one third of the distance along the push rod from the vibrator 1 to the upper specimen holder 10.

In an alternative embodiment, which is not shown, the lower specimen holder 15 is induced to oscillate in a direction generally perpendicular to the linear oscillation of the push rod 9 and upper specimen holder 10. This produces a similar effect of a compound multi-directional relative movement between the upper specimen 13 and the lower specimen 14. The lower specimen holder 15 can be induced to move on its own with the heating block 16, or alternatively the heating block 16 and holder 15 may be moved together.

The temperature regulating block 16 contains electric heaters or cooling elements which together with thermocouple 25 and a suitable controller allow tests to be carried out at elevated temperatures or reduced temperatures. The temperature regulating block 16 is attached to a flexural support 20 which is designed to be stiff in all directions except the direction of oscillation of the upper sample 13, in which direction it is allowed to deflect. The motion of the temperature regulating block 16 and lower sample holder 15 in this direction is restrained by the force transducer 21 attached to a rigid block 22.

Suitably the lower, (usually) fixed specimen holder may be in the form of a stainless steel bath to contain the test lubricant. The specimen holder may be attached to a block containing electrical heaters and/or galleries for cooling fluids which together with suitable control means will allow tests to be carried out at temperatures other than room temperature. The specimen holder may also be enclosed in a chamber to allow tests to be carried out in specific gas atmospheres. Suitably the apparatus further comprises means for applying a variable known load to press the specimens into contact.

Since the force transducer 21, for example a piezo electric force transducer, is many orders of magnitude stiffer than the flexural support 20 in the direction of oscillation of the upper sample 13 the frictional forces between the specimens will be reacted almost entirely against the force transducer 21. The force transducer 21 is connected to an electronic circuit which provides instantaneous and time averaged friction force outputs. By means of this apparatus it is also possible to measure the electrical resistance of the contact between the two specimens. This resistance is determined by the degree of asperity to asperity contact between the specimens and is a qualitative measure of the effectiveness of the lubricant at separating the specimens.

During these measurements it is possible to vary the parameters of load and specimen temperature by the methods described above.

COMPONENT LIST

1—Electromagnetic Vibrator
2—Supports
3—Bearings
4—Rear Flexure
5—Forward Flexure
6—Threaded Collar
7—Linear Variable Differential Transformer (LVDT)
8—Core
9—Push Rod
10—Upper Specimen Holder
11—Load Pin
12—Grub Screw
13—Upper Specimen
14—Lower Specimen
15—Lower Specimen Holder
16—Heater Block
17—Screws
18—Screws
19—Screws
20—Flexural Support
21—Force Transducer
22—Rigid Block
23—Base Block 24—Housing
25—Thermocouple
26—feedback control circuit
27—Counter Weight

The invention claimed is:

1. A test apparatus for measuring the frictional properties of a fluid comprising; a first specimen holder which is adapted to hold a first specimen in the fluid being tested, such that a first specimen surface of the first specimen is in contact with a second specimen surface of a second specimen, in a second specimen holder, means for applying a measurable load between the two specimens, said test apparatus also comprising oscillatory driving means for oscillating at least one of the specimen holders along a first direction, wherein the apparatus includes a motion inducing means, for inducing a motion between the first and second specimen holders in a second direction, wherein the first specimen holder is connected to a shaft which is induced to move in the first direction being the direction of the length of the shaft, wherein the motion inducing means for inducing a motion in a second direction is an off-centre counter weight located on the shaft, and the motion inducing means induces a compound movement of the upper specimen holder relative to the lower specimen holder in both an axial direction parallel to the length of the shaft and in a non-axial direction.

2. A test apparatus according to claim 1, wherein the first specimen holder is connected to the oscillatory driving means and the second specimen holder is connected to the motion inducing means.

3. A test apparatus according to claim 1, wherein the test apparatus comprises displacement measuring means to determine an amplitude of oscillation of the specimen.

4. A test apparatus according to claim 3, further comprising a means of controlling the amplitude of oscillation of the specimen.

5. A test apparatus according to claim 1, further comprising a force measuring means to measure a frictional force between the first and second specimens.

6. A test apparatus according to claim 4, wherein the displacement measuring means is a linear variable differential transformer.

7. A test apparatus according to claim 4, wherein the displacement measurement means is connected to a feedback circuit to control an amplitude of vibration of the oscillatory driving means.

8. A test apparatus according to claim 1, wherein the oscillatory driving means is variable in frequency and amplitude.

9. A test apparatus according to claim 1, wherein at least one of the test specimens is provided in a tank for containing a test lubricant.

10. A test apparatus according to claim 1, further comprising a temperature regulating means in order to carry out tests at various temperatures.

11. A test apparatus according to claim 1, wherein the first and second specimens are electrically insulated from each other when they are not in contact and that the test apparatus further comprises a means of measurement of the electrical resistance between the test specimen and the test surface.

12. A method for measuring the frictional properties of a fluid comprising;
  providing a first specimen holder connected to a shaft to hold a first specimen in the fluid being tested, such that a first specimen surface of the first specimen is in contact with a second specimen surface of a second specimen, in a second specimen holder,
  applying a measurable load between the two specimens, oscillating at least one of the specimen holders along a first direction,
  measuring the extent of wear on the first or second sample, and
  inducing a motion between the first and second specimen holders in a second direction; wherein inducing the motion includes inducing a compound movement of the upper specimen holder relative to the lower specimen holder in both an axial direction parallel to the shaft and in a non-axial direction.

* * * * *